United States Patent [19]

Portas

[11] Patent Number: 5,005,736
[45] Date of Patent: Apr. 9, 1991

[54] APPARATUS FOR SIMULTANEOUSLY DISPENSING TWO COMPONENTS

[76] Inventor: Abelardo A. Portas, Arcos 2757 - 1 piso "E", 1428 Buenos Aires, Argentina

[21] Appl. No.: 517,505

[22] Filed: Apr. 30, 1990

Related U.S. Application Data

[63] Continuation of Ser. No. 261,370, Oct. 24, 1988, abandoned.

[30] Foreign Application Priority Data

Oct. 23, 1987 [AR] Argentina ............................... 309102

[51] Int. Cl.⁵ ............................................. B67D 5/56
[52] U.S. Cl. .................................. 222/135; 222/129; 222/173; 222/506; 239/306
[58] Field of Search .......................................... 222/173

[56] References Cited

U.S. PATENT DOCUMENTS

| 3,045,925 | 7/1962 | Giangualano | 239/306 |
| 3,127,070 | 3/1964 | Brickman | 222/506 |
| 3,303,970 | 2/1967 | Breslau et al. | 222/135 |
| 3,416,709 | 12/1968 | Shultz et al. | 239/306 |
| 3,506,159 | 4/1970 | Muller | 222/402.13 |
| 3,575,319 | 4/1971 | Safianoff | 239/304 |
| 4,496,081 | 1/1985 | Farrey | 222/135 |
| 4,773,562 | 9/1988 | Gueret | 222/135 |
| 4,792,062 | 12/1988 | Goncalves | 222/135 |
| 4,826,048 | 5/1989 | Skorka et al. | 239/306 |
| 4,880,143 | 11/1989 | Murray et al. | 222/135 |
| 4,902,281 | 2/1990 | Avoy | 222/137 |

FOREIGN PATENT DOCUMENTS 416340 6/1966 Switzerland ........................ 239/304

Primary Examiner—H. Grant Skaggs
Assistant Examiner—Steven Rim
Attorney, Agent, or Firm—Kenyon & Kenyon

[57] ABSTRACT

An apparatus is provided with has a support frame in which a pair of pressurized containers is mounted. A common pressure plate is fitted over the push button valve of the containers and a single key is used for actuating the push button valves. Each valve is directed on an axis towards a common point so as to create a fog or cloud containing insecticide and/or fungicide.

11 Claims, 2 Drawing Sheets

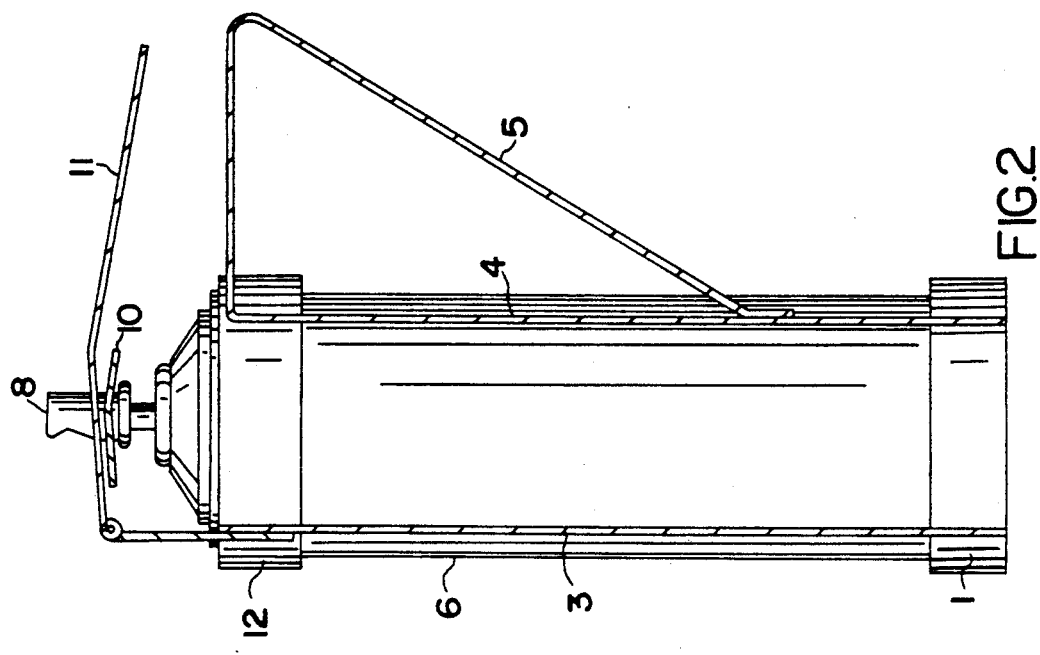
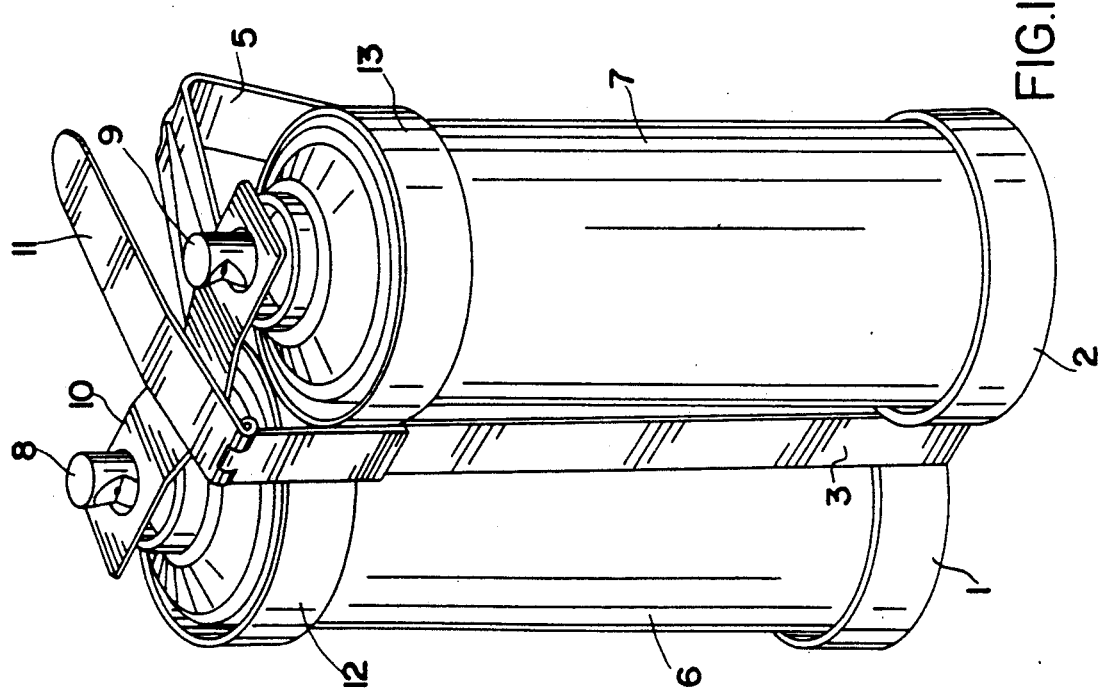

APPARATUS FOR SIMULTANEOUSLY DISPENSING TWO COMPONENTS

This application is a continuation of application Ser. No. 07/261,370, filed Oct. 24, 1988 now abandoned.

The present invention relates to a process for forming insecticide and/or fungicide clouds and to an apparatus for carrying performing same.

A process is known in which one incorporates in silicon tetrachloride a substance from the group consisting of the pesticides, insecticides, fungicides, herbicides and/or mixtures thereof, and atomizes the resulting mixture by means of a stream of inert gas to which ammonia and/or nitrogenated compounds have been added.

Briefly, the invention provides a process including the steps of producing a first atomized stream of a compound made up, per 100 cc, of between 28 and 42 cc liquid ammonia of 26° Beaume, between 0.8 and 1.2 cc demineralized water, and between 24 and 36 cc propellant; producing, simultaneously with the first stream, a second atomized stream of a compound which comprises, per 100 cc, between 12 and 18 cc $SiCl_4$, between 3.2 and 4.8 cc $CCl_4$, between 0.8 and 1.2 g silver iodide, between 12 and 18 cc solvents, between 12 and 18 cc of a substance of the group of the insecticides, fungicides or mixture thereof and between 40 and 60 cc propellant; directing both streams toward the same point and causing them to collide.

In addition, the invention provides an apparatus for performing the process. This apparatus includes a support frame for receiving a pair of pressurized containers in side-by-side relation, a handle secured to one side of the frame, a pressure plate having a pair of apertures, each of which is sized to fit over an actuating push button of an atomizing valve on a respective container and a key hingedly mounted on the frame for disposition over the pressure plate between the apertures and the handle in order to permit pressing of the pressure plate towards the containers for simultaneous actuation of the valves of the containers.

The containers which are used are characterized in that each has an atomizing valve at an upper end and an actuating push button for actuating the valve. In addition, each push button has an outlet orifice disposed on an axis directed to a common point of intersection with the axis of the orifice of the other push button.

Upon actuation of the apparatus, that is, by pressing the key onto the pressure plate, the valves of the two containers are actuated so as to direct a respective atomized stream of a respective compound to the common point in order to create a fog or cloud of insecticide and/or fungicide.

So that the invention can be easily understood and carried into effect in a simple manner, the apparatus for carrying out the process of the invention has been represented in its preferred form of realization in the attached drawings in which:

FIG. 1 is a perspective view of an apparatus in accordance with the invention.

FIG. 2 is a view in side elevation of the apparatus illustrated in FIG. 1 and

In all figures like or corresponding parts of the apparatus for carrying out the invented process are indicated with the same references.

Figure 3:
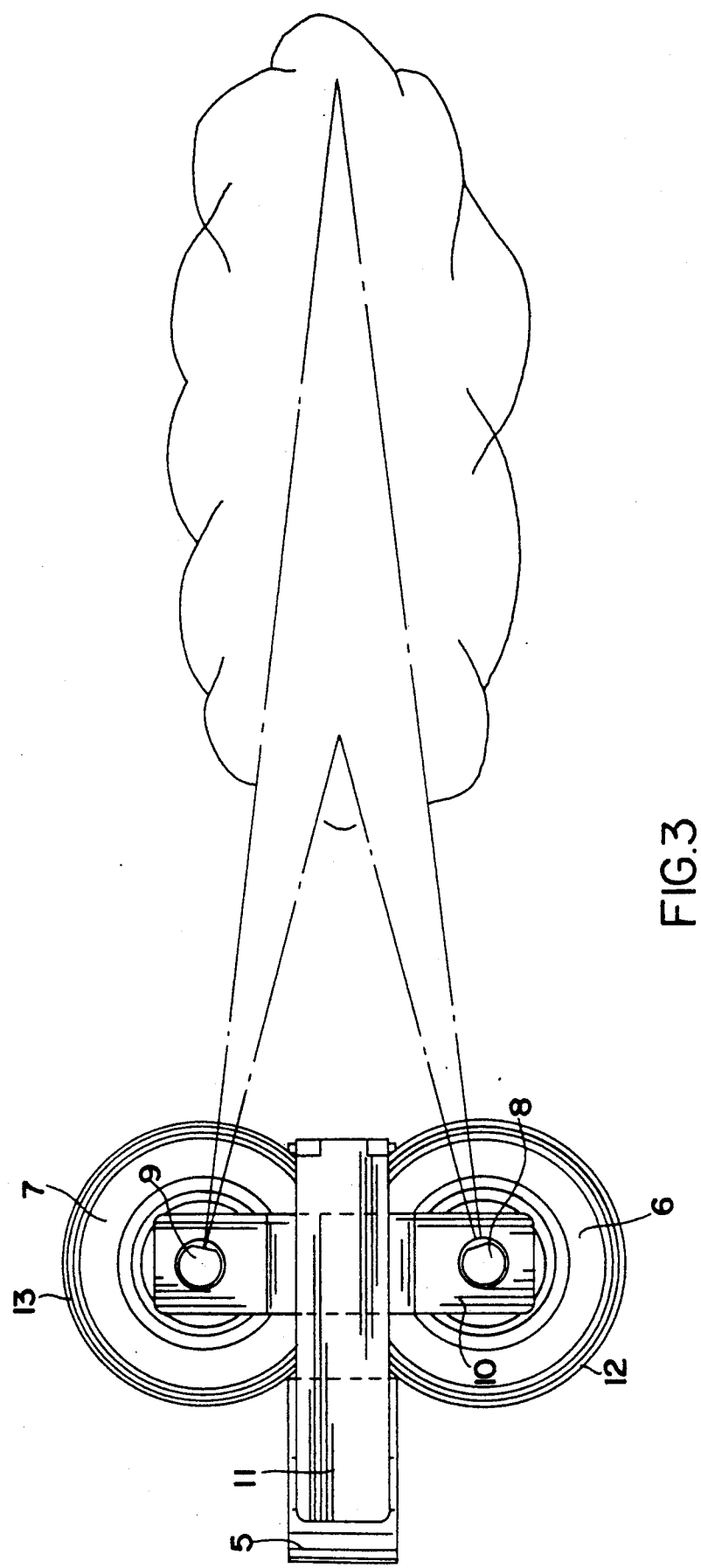
FIG. 3 is a plan view of the apparatus illustrated in the preceding FIG.

Basically the invented process produces a fog of hydrated silica particles carrying an insecticide, fungicide or mixture of both, with an associated fog of ammonium chloride particles also partially carrying insecticide, fungicide or mixture of both.

The basic fog, that is, without insecticide, fungicide or mixture of both, is produced by the simultaneous interaction of silicon tetrachloride ($SiCl_4$) with water vapor and ammonia, as follows:

$$SiCl_4 + 2H_2O \text{ (as vapor)} \rightarrow SiO_2 \text{ (hydrated)} + 4HCl$$

$$4HCl + 4NH_3 \text{ (gas)} \rightarrow 4NH_4Cl$$

The two reactions take place simultaneously, mainly in the vapor phase, so that practically they can be reduced to the following reaction $$SiCl_4 + 4NH_3 + 2H_2O \rightarrow 4NH_4Cl + SiO_2$$

As the materialization of the production of the reaction causes the major part thereof to take place in the vapor phase, there forms a cloud or fog (or rather a vaporization) of finely divided particles of $SiO_2$ and $NH_4Cl$, which particles are approximately in the order of 15 microns.

In exhaustive tests and experimentations it has been found that the best practical results are obtained when about 1 part of commercial $SiCl_4$ is reacted with 1 ½ part of a 10% ammonia solution. Considering that the commercial grade of $SiCl_4$ can be about 90% pure, one concludes that the practical tests are very close to the theoretical quantities for producing a "neutral" fog with a small proportion of ammonia or residual hydrochloric acid.

The heavier constituent of the fog is the ammonium chloride, present therein at approximately 78% by weight. The $SiO_2$ represents 22% of said fog.

Nevertheless, as the $SiO_2$ is probably in the form of hydrated silica (the simplest form, $H_2SiO_3$), it may be assumed, practically, that the weights of the particles are in a relation of 3 parts $NH_4Cl$ to one part $SiO_2$.

In the actual operation, the insecticide, fungicide or their mixture is mixed with the $SiCl_4$ in the liquid state and evaporated with the $SiCl_4$ as the reaction in fog takes place. The insecticide, fungicide or their mixture is then bound to the particles of $NH_4Cl$ and $SiO_2$ by occlusion, absorption and surface adhesion and is transported with the fog to the desired places.

Based on the well known properties of absorption and adsorption of hydrated silica, a large part of the insecticide, fungicide or their mixture is transported by the siliceous part of the fog more than by the ammonium chloride, although their weights in the fog are in inverse relation. But in any event, the vehicle for the insecticide, pesticide or their mixture are the fog particles, rather than the fumes or vapor of those substances in themselves.

It can be theorized additionally that the new, original and unexpected results of the high and immediate lethal effect for insects, as well as the immediate residual effect, obtained with the invention, are due to the fact that the soluble ammonium chloride particles easily release a large proportion of the insecticide, fungicide or their mixture, on first contact, to produce the immediate lethal effect and that that of the pores of the silica (sic) on adhering to the surfaces of the insects and the surrounding zones.

Besides, since the insecticide, fungicide or their mixture is "part"0 of the fog particle and can deposit only when said particles do so, it can be affirmed that when the insecticide, fungicide or their mixture deposits or settles anywhere, the fog does so also and vice versa and the insecticide, pesticide, or their mixture, evidently, cannot isolate themselves and remain in close vicinity to the sprayer or nebulizer.

For a correct formation of this dense ammonium chloride fog, ideally it should not dissipate quickly, that is, it should be stable for the longest possible time, independently of the ambient relative humidity of the place where it is applied.

To this end there is added to the liquid ammonia compound ethyleneglycol, propanotriol and sodium chloride, because of their highly hygroscopic and surface active properties, which permits greater absorption of the ambient relative humidity by the ammonium chloride particles to form a denser fog and after its formation retaining the insecticide, fungicide or their mixture contained in said ammonium chloride particles by absorption, adsorption or surface tension, preventing the insecticide, fungicide or their mixture from volatilizing and rising, dissipating into the atmosphere. Furthermore, as ethyleneglycol has specific physical-chemical properties, being soluble in water and acting as antifreeze, it favors the formation of the fog on cold days with low temperatures (close to 0° C.). Also, the presence of propanotriol favors and improves the properties of the microdrops or "dew", by its hygroscopicity and surface tension, imparting to the fog the necessary specific gravity or density for it to stay as long as possible, avoiding its rapid dissipation, and therefore improving its insecticidal and/or fungicidal activity over the longest exposure time and favoring the surface phenomena, absorption and adsorption by contact of the active principle (insecticide, fungicide or their mixture).

The addition to the $SiCl_4$ of carbon tetrachloride and silver iodide, due to their specific qualities of acting as nuclei of condensation, forming(sic) larger fog particles by coalescence, etc. and therefore acting as submerging factor when combining with the sodium chloride and the propanotriol. Besides the $C.Cl_4$ forms with the $SiCl_4$ a real ideal solution since from the physical-chemical point of view these liquids, when mixed homogeneously, give neither volume variation (expansion or contraction) nor temperature variation, so that the physical properties such as index of refraction, fluidity and vapor tension are optimum, maintaining the insecticidal and/or fungicidal effect stable in the microdrops or dew forming a micromolecular film by the fluidizing action of the solvents and propellants/propane, butane or freon.

For a perfect result of the process it is absolutely necessary that the liquid ammonia and its admixtures and the $SiCl_4$ and its admixtures be expelled from their containers simultaneously so as not to allow one of them to issue alone, because of the molestations that the ammonia or chloride vapors could cause indiscriminately.

We give as example of realization the following in one of its possibilities. A first atomized stream was produced of a compound composed per 100 cc by

| Liquid ammonia 26° Beaume | 35 cc |
| --- | --- |
| Ethyleneglycol | 1 cc |
| Propanotriol | 5 cc |
| Sodium chloride | 5 g |
| Ethanol | 4 cc |

-continued

| Demineralized water | 20 cc |
| --- | --- |
| Propellant | 30 cc |

A second atomized stream was produced of a compound composed per 100 cc by

| $SiCl_4$ | 15 cc |
| --- | --- |
| $C Cl_4$ | 4 cc |
| Silver iodide | 1 g |
| Solvents | 15 cc |
| Insecticide, fungicide or their mixture | 15 cc |
| Propellant | 50 cc |

Both streams were produced simultaneously and were directed toward the same point causing them to rise together to form a cloud.

Of the various insecticide compounds only the natural or synthetic pyrethrins such as permethrin, tetramethrin, cypermethrin, landacihalothrin, sumethrin, pralethrin, D-allethrin, D-empethrin, D-phenothrin, detamethrin, etc. can be utilized with real effectiveness by the process of the invention, as the quantity that must be used is very small compared with the chlorinated or phosphorated insecticides. For example, comparing the doses needed per hectare to combat cotton boll weevil (helicoverpa gelotopocon) it is for

| chlorinated insecticides | 1000 cc |
| --- | --- |
| phosphorated insecticides | 900 cc |
| pyrethrin | 4 to 12 cc |

This shows that small quantities of pyrethrins produce great effects, being suitable for use in the process of the invention.

The apparatus for carrying out the process of the invention comprises a support frame preferably formed by a pair of interconnected bases 1, 2, a pair of uprights 3, 4 facing each other and joined by one of their ends to said bases, and a handle 5 extending from the upright 4.

On each of the bases 1, 2 rests the bottom of a corresponding container 6, 7 for each of the compounds generating the first and second of the abovementioned streams, each container being provided with an atomizing valve actuated by a pushbutton 8, 9. The outlet orifice of each pushbutton, preferably of a diameter between 0.30 and 0.55 mm, has an axis directed toward the same cross point, as shown according to different variants by broken lines in FIG. 3, so that the first and second generated streams collide at the point of convergence of the axes giving rise to the formation of the cloud as has been explained.

Both pushbuttons are united by a pressure plate 10, on which rests an actuating key 11, hinged by one of its ends to the free end of the upright, the frame being completed with the pair of guide rings of the containers, which rings are marked with the references 12, 13. .

By pressure on the free end of key 11, the pushbuttons 8 and 9 will be depressed simultaneously, the first and second streams being generated in unison, an essential condition we have already pointed out, for them to give rise to the formation of the insecticide and/or fungicide cloud as they converge at the common point of intersection of their axes, as has been explained.

I claim:

1. An apparatus comprising a support frame for receiving a pair of pressurized containers in side-by-side relation;

a handle secured to one side of said frame;

a pressure plate having a pair of apertures, each aperture being sized to fit over an actuating push button of an atomizing valve on a respective container with an outlet orifice of each push button above said pressure plate and a key hingedly mounted on said frame opposite said handle for disposition over said pressure plate between said apertures and said handle to permit pressing of said pressure plate towards the containers for simultaneous actuation of the valves of the containers.

2. An apparatus as set forth in claim 1 wherein said frame includes a pair of bases to receive a pair of containers, a pair of uprights secured to said bases, and a pair of guide rings secured to said uprights for guiding the containers therethrough.

3. An apparatus as set forth in claim 2 wherein said key in hingedly connected to one of said uprights.

4. In combination a support frame;

a pair of pressurized containers disposed in side-by-side relation in said frame, each container having an atomizing valve at an upper end and an actuating push button having an unobstructed outlet orifice disposed on an axis directed to a common point of intersection with said axis of said orifice of the other push button;

a pressure plate having a pair of apertures fitting over said push buttons with said outlet orifices being above said pressure plate; and a key hingedly mounted on said frame for pressing said pressure plate towards said containers for simultaneous actuation of said valves.

5. The combination as set forth in claim 4 wherein said frame includes a pair of bases to receive a pair of containers, a pair of uprights secured to said bases, and a pair of guide rings secured to said uprights for guiding the containers therethrough.

6. The combination as set forth in claim 5 wherein said key is hingedly connected to one of said uprights.

7. The combination as set forth in claim 4 which further comprises a handle secured to said frame in alignment with said key.

8. In combination a support frame;

a pair of pressurized containers disposed in side-by-side relation in said frame, each container having an atomizing valve at an upper end and an actuating push button having an unobstructed outlet orifice disposed on an axis directed to a common point of intersection with said axis of said orifice of the other push button;

a pressure plate having an upper surface mounted below said outlet orifices and having a pair of apertures removably fitted over said push buttons and resting on said push buttons; and a key hingedly mounted on said frame for pressing said pressure plate towards said containers for simultaneous actuation of said valves to emit simultaneous atomized streams for mixing and producing a cloud at said common point.

9. The combination as set forth in claim 8 wherein one of said containers includes a compound composed, in part, of liquid ammonia and the other of said pressurized containers includes a compound composed in part of silicon tetrachloride.

10. The combination as set forth in claim 9 wherein said other container includes at least one of an insecticide and a fungicide.

11. The combination as set forth in claim 8 wherein each outlet orifice has a diameter between 0.30 and 0.55 millimeters.

* * * * *

UNITED STATES PATENT AND TRADEMARK OFFICE
CERTIFICATE OF CORRECTION

PATENT NO. : 5,005,736
DATED : April 9, 1991
INVENTOR(S) : ABELARDO A. PORTAS

It is certified that error appears in the above-identified patent and that said Letters Patent is hereby corrected as shown below:

```
Column 1, line 65 change "Fig." to -figures-
Column 2, line 28 change "1" (bold) to -1- (not bolded)
Column 2, line 43 change ", 1 fungicide" to -, fungicide-
Column 3, line 2 delete "0"
Column 5, line 8 change "plate and" to -plate; and-
```

Signed and Sealed this

Sixth Day of October, 1992

Attest:

DOUGLAS B. COMER

Attesting Officer     Acting Commissioner of Patents and Trademarks